(12) United States Patent
Kitamoto et al.

(10) Patent No.: US 10,513,479 B2
(45) Date of Patent: Dec. 24, 2019

(54) METHOD OR PRODUCING HYDROHALOFLUOROOLEFINS (71) Applicant: Central Glass Company, Limited, Ube-shi, Yamaguchi (JP)

(72) Inventors: Takamasa Kitamoto, Saitama (JP); Satoru Okamoto, Saitama (JP); Masahiko Tani, Saitama (JP); Masatomi Kanai, Saitama (JP); Kohei Sumida, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 15/578,405

(22) PCT Filed: May 27, 2016

(86) PCT No.: PCT/JP2016/065670
§ 371 (c)(1),
(2) Date: Nov. 30, 2017

(87) PCT Pub. No.: WO2016/194794
PCT Pub. Date: Dec. 8, 2016

(65) Prior Publication Data
US 2018/0215689 A1    Aug. 2, 2018

(30) Foreign Application Priority Data

Jun. 2, 2015  (JP) .................................. 2015-112429
May 10, 2016  (JP) .................................. 2016-094431

(51) Int. Cl.
*C07C 17/358*    (2006.01)
*C07C 21/18*    (2006.01)
(Continued)

(52) U.S. Cl.
CPC ............. *C07C 17/358* (2013.01); *B01J 21/04* (2013.01); *B01J 21/066* (2013.01); *B01J 27/125* (2013.01); *B01J 27/135* (2013.01); *B01J 37/26* (2013.01)

(58) Field of Classification Search
CPC ........................... C07C 17/358; C07C 17/389
See application file for complete search history.

(56) References Cited

U.S. PATENT DOCUMENTS

| 4,535,194 A | 8/1985 | Woodard |
| 6,403,847 B1 | 6/2002 | Nakada et al. |

(Continued)

FOREIGN PATENT DOCUMENTS

| JP | 60-36429 A | 2/1985 |
| JP | 2000-95714 A | 4/2000 |

(Continued)

OTHER PUBLICATIONS

International Search Report (PCT/ISA/210) issued in PCT Application No. PCT/JP2016/065670 dated Aug. 16, 2016 with English-language translation (Five (5) pages).

(Continued)

*Primary Examiner* — Medhanit W Bahta
(74) *Attorney, Agent, or Firm* — Crowell & Moring LLP (57) ABSTRACT

A method for isomerizing a hydrohalofluoroolefin isomer to produce a corresponding hydrohalofluoroolefin isomer includes a step contacting a composition that contains at least a hydrohalofluoroolefin isomer and that has been adjusted to 100 ppm or lower in moisture concentration, with a catalyst in a gas phase, thereby obtaining a product. This method makes it possible to suppress the catalyst performance lowering.

25 Claims, 3 Drawing Sheets

(51) Int. Cl.
*B01J 27/125* (2006.01)
*B01J 27/135* (2006.01)
*B01J 37/26* (2006.01)
*B01J 21/04* (2006.01)
*B01J 21/06* (2006.01)

(56) References Cited

U.S. PATENT DOCUMENTS

| | | | |
|---|---|---|---|
| 8,410,324 | B2 | 4/2013 | Sharratt et al. |
| 8,513,473 | B2 | 8/2013 | Sakyu et al. |
| 9,115,044 | B2 | 8/2015 | Okamoto et al. |
| 9,255,046 | B2 | 2/2016 | Cottrell et al. |
| 9,365,472 | B2 | 6/2016 | Okamoto et al. |
| 2010/0185028 | A1 | 7/2010 | Okamoto |
| 2010/0197980 | A1 | 8/2010 | Nappa |
| 2013/0253234 | A1* | 9/2013 | Nappa ............... C07C 17/358 570/151 |
| 2014/0228600 | A1* | 8/2014 | Elsheikh ............ C07C 17/38 570/160 |
| 2014/0305161 | A1 | 10/2014 | Kawaguchi et al. |
| 2014/0336424 | A1* | 11/2014 | Okamoto ............ C07C 17/358 570/151 |
| 2015/0112103 | A1* | 4/2015 | Okamoto ............ C07C 17/358 570/151 |
| 2016/0272560 | A1* | 9/2016 | Chiu .................. C07C 17/389 |

FOREIGN PATENT DOCUMENTS

| | | |
|---|---|---|
| JP | 2009-108049 A | 5/2009 |
| JP | 2010-83818 A | 4/2010 |
| JP | 2010-523635 A | 7/2010 |
| JP | 2010-536777 A | 12/2010 |
| JP | 2013-107848 A | 6/2013 |
| JP | 2014-28799 A | 2/2014 |
| JP | 2015-44814 A | 3/2015 |
| WO | WO 94/02243 A1 | 2/1994 |
| WO | WO 2008/008351 A2 | 1/2008 |
| WO | WO 2008/030443 A1 | 3/2008 |
| WO | WO 2010/082662 A1 | 7/2010 |
| WO | WO 2013/099856 A1 | 7/2013 |

OTHER PUBLICATIONS

Japanese-language Written Opinion (PCT/ISA/237) issued in PCT Application No. PCT/JP2016/065670 dated Aug. 16, 2016 (Three (3) pages).

English Translation of document C1 (Japanese-language Office Action issued in counterpart Japanese Application No. 2016-094431 dated Apr. 4, 2017) previously filed on Nov. 30, 2017 (five (5) pages).

\* cited by examiner

METHOD OR PRODUCING HYDROHALOFLUOROOLEFINS

TECHNICAL FIELD

The present invention relates to a method for producing hydrohalofluoroolefins.

BACKGROUND TECHNOLOGY

Many hydrohalofluoroolefins can exist as E/Z isomers according to the arrangement of substituents around the double bond. In general, E/Z isomers have different physical characteristics and chemical characteristics. Therefore, in particular uses, one isomer may be preferable to the other. From this, in some cases, it is preferable to be able to convert one E/Z isomer to the other E/Z isomer.

Under such background, there have been tried mutual conversions by isomerization of hydrohalofluoroolefins. It is described in Patent Publication 1 that the ratio of cis isomer to trans isomer of 1,2,3,3,3-pentafluoropropene can be increased and decreased and that this can be conducted by using a catalyst supported on $AlF_3$ or carbon. This catalyst is selected from $SbCl_wF_{5-w}$, $TiCl_xF_{4-x}$, $SnCl_yF_{4-y}$, and $TaCl_zF_{5-z}$, wherein w is 0-4, x is 0-3, y is 0-3, and z is 0-4. Furthermore, in Patent Publication 2, there is described a partial isomerization from E-1,3,3,3-tetrafluoropropene to Z-1,3,3,3-tetrafluoropropene on a crushed, chromium oxide gel pellets catalyst.

In Patent Publication 3, there is disclosed a process in which a catalyst, such as a Lewis acid catalyst or a chromia-containing catalyst, is contacted with a E-(hydro)halofluoroalkene, thereby isomerizing the same into the Z-(hydro)halofluoroalkene by using an equilibrium reaction.

In Patent Publication 4, there is disclosed a method for producing Z-1,3,3,3-tetrafluoropropene from E-1,3,3,3-tetrafluoropropene by using a metal-containing, metal compound, etc. as the catalyst.

In Patent Publication 5, there is disclosed a method for producing E-1,3,3,3-tetrafluoropropene from Z-1,3,3,3-tetrafluoropropene by using a metal oxide, its partially fluorinated compound, or its totally fluorinated compound, etc. as the catalyst.

PRIOR ART PUBLICATIONS

Patent Publications

Patent Publication 1: International Publication WO 2008/008351
Patent Publication 2: International Publication WO 2008/030443
Patent Publication 3: JP Patent Application Publication 2010-523635
Patent Publication 4: JP Patent Application Publication 2014-28799
Patent Publication 5: JP Patent Application Publication 2009-108049

DISCLOSURE OF THE INVENTION

Task to be Solved by the Invention

It is a task of the present invention to provide a method for suppressing lowering of catalyst performance in a method for efficiently isomerizing a hydrohalofluoroolefin isomer (isomer 1) to produce the corresponding hydrohalofluoroolefin isomer (isomer 2).

Means for Solving the Task

The present inventors have conducted an eager study to solve the task. As a result, we found that, in an isomerization of a hydrohalofluoroolefin by its contact with a catalyst, it is possible to suppress the catalyst performance lowering by controlling the concentration of moisture that can be contained in the hydrohalofluoroolefin to a predetermined concentration or lower, thereby completing the present invention.

That is, the present invention contains each invention of the following.

[Invention 1]
A method for isomerizing a hydrohalofluoroolefin isomer (isomer 1) to produce a corresponding hydrohalofluoroolefin isomer (isomer 2), comprising step 1 of contacting a composition that contains at least a hydrohalofluoroolefin isomer (isomer 1) and that has been adjusted to 100 ppm or lower in moisture concentration, with a catalyst in a gas phase, thereby obtaining a product.

[Invention 2]
The method according to Invention 1, wherein there is used a composition that contains at least a hydrohalofluoroolefin isomer (isomer 1) and that has been adjusted to 50 ppm or lower in moisture concentration.

[Invention 3]
The method according to Invention 1 or 2, wherein the contacting is conducted at a temperature of 0 to 600° C. with a contact time of 0.01 to 500 seconds.

[Invention 4]
The method according to Invention 1 or 2, wherein the contacting is conducted at a temperature of 20 to 550° C. with a contact time of 1 to 150 seconds.

[Invention 5]
The method according to Invention 3 or 4, wherein the temperature and the contact time are in a trade-off relation.

[Invention 6]
The method according to any of Inventions 1 to 5, wherein the catalyst is a metal oxide containing at least one metal selected from the group consisting of aluminum, chromium, titanium, manganese, iron, nickel, cobalt, copper, magnesium, zirconium, molybdenum, zinc, tin, lanthanum, niobium, tantalum, and antimony.

[Invention 7]
The method according to any of Inventions 1 to 5, wherein the catalyst is a metal fluorinated compound that has been partially or totally fluorinated and that contains at least one metal selected from the group consisting of aluminum, chromium, titanium, manganese, iron, nickel, cobalt, copper, magnesium, zirconium, molybdenum, zinc, tin, lanthanum, niobium, tantalum, and antimony.

[Invention 8]
The method according to any of Inventions 1 to 5, wherein the catalyst is a supported catalyst that supports a metal compound containing at least one metal selected from the group consisting of aluminum, chromium, titanium, manganese, iron, nickel, cobalt, copper, magnesium, zirconium, molybdenum, zinc, tin, lanthanum, niobium, tantalum, and antimony.

[Invention 9]
The method according to any of Inventions 6 to 8, wherein the catalyst is a catalyst that has been further subjected to a fluorination treatment.

[Invention 10]
The method according to any of Inventions 1 to 9, wherein the hydrohalofluoroolefin isomer (isomer 1) is a hydrohalofluoroolefin containing two to six carbons.

[Invention 11]
The method according to any of Inventions 1 to 10, wherein the hydrohalofluoroolefin isomer (isomer 1) is a hydrohalofluoroolefin represented by the following general formula (1).

$$(CX^1X^2X^3)CX^4=CX^5X^6 \quad (1)$$

(In the general formula (1), each of $X^1$ to $X^6$ is independently H, F, Cl or Br, and, of $X^1$ to $X^6$, one to five of them are fluorines, the rest is H, Cl or Br, and at least one of them is H.)

[Invention 12]
The method according to any of Inventions 1 to 11, wherein the hydrohalofluoroolefin isomer (isomer 1) is 1-chloro-3,3,3-trifluoropropene, 1,2-dichloro-3,3,3-trifluoropropene, 1,3,3,3-tetrafluoropropene, 1-chloro-1,3,3,3-tetrafluoropropene, 2-chloro-1,3,3,3-tetrafluoropropene, 1-chloro-2,3,3,3-tetrafluoropropene, or 1,2,3,3,3-pentafluoropropene.

[Invention 13]
The method according to any of Inventions 1 to 12, further comprising step 2 of removing an acid component from the product obtained by step 1 and then separating the hydrohalofluoroolefin isomer (isomer 2) from the product from which the acid component has been removed.

[Invention 14]
The method according to any of Inventions 1 to 13, further comprising:
step 3 of removing an acid component from the product obtained by step 1 and then separating a composition that contains at least the hydrohalofluoroolefin isomer (isomer 1) from the product from which the acid component has been removed; and
step 4 of reusing the composition that contains at least the hydrohalofluoroolefin isomer (isomer 1) and that has been separated by step 3, as the composition containing at least the hydrohalofluoroolefin isomer (isomer 1) of step 1.

[Invention 15]
The method according to any of Inventions 1 to 14, wherein the moisture concentration adjustment is conducted by distilling the composition containing at least the hydrohalofluoroolefin isomer (isomer 1), or by contacting the composition containing at least the hydrohalofluoroolefin isomer (isomer 1) with a dehydrating agent, or by both of the distilling and the contacting.

[Invention 16]
The method according to Invention 15, wherein the moisture concentration adjustment is conducted by distilling the composition containing at least the hydrohalofluoroolefin isomer (isomer 1), and, at least prior to the distillation, contacting the composition containing at least the hydrohalofluoroolefin isomer (isomer 1) with a dehydrating agent.

[Invention 17]
A method for contacting a hydrohalofluoropropene isomer (isomer 1) represented by the general formula (3) with a catalyst to produce a corresponding hydrohalofluoropropene isomer (isomer 2), comprising contacting a composition that contains at least a hydrohalofluoropropene isomer (isomer 1) and that has been adjusted to 100 ppm or lower in moisture concentration, with a catalyst in a gas phase at a temperature of 0 to 600° C. with a contact time of 0.01 to 500 seconds.

$$CF_3CH=CHX^7 \quad (3)$$

(In the general formula (3), $X^7$ is F or Cl.)

[Invention 18]
The method according to Invention 17, wherein the catalyst is a metal fluorinated compound that has been partially or totally fluorinated and that contains at least one metal selected from the group consisting of aluminum, chromium, titanium, manganese, iron, nickel, cobalt, copper, magnesium, zirconium, molybdenum, zinc, tin, lanthanum, niobium, tantalum, and antimony.

[Invention 19]
The method according to Invention 17 or 18, wherein the hydrohalofluoropropene isomer (isomer 1) represented by the general formula (3) is E isomer, and wherein the contacting is conducted at a temperature of 200 to 550° C. with a contact time of 0.1 to 250 seconds.

[Invention 20]
The method according to Invention 17 or 18, wherein the hydrohalofluoropropene isomer (isomer 1) represented by the general formula (3) is Z isomer, and wherein the contacting is conducted at a temperature of 50 to 300° C. with a contact time of 15 to 200 seconds.

[Invention 21]
The method according to Invention 19 or 20, wherein the temperature and the contact time are in a trade-off relation.

[Invention 22]
A composition that contains at least a hydrohalofluoroolefin isomer (isomer 1), that has been adjusted to 100 ppm or lower in moisture concentration, and that is used to be contacted with a catalyst in a gas phase to isomerize the hydrohalofluoroolefin isomer (isomer 1), thereby producing a corresponding hydrohalofluoroolefin isomer (isomer 2).

[Invention 23]
A method for isomerizing a hydrohalofluoroolefin isomer (isomer 1) by a contact with a catalyst in a gas phase to produce a corresponding hydrohalofluoroolefin isomer (isomer 2), comprising adjusting a moisture concentration of a composition containing at least a hydrohalofluoroolefin isomer (isomer 1) to 100 ppm or lower and then supplying the composition to an isomerization reaction system.

As disclosed in the present description, it was found that the amount of moisture that can be brought into the reaction system is greatly involved in lowering of catalyst performance. This is not described nor suggested in Patent Publications 1 to 5.

In the present description, "isomerization" means the change of E isomer/Z isomer ratio before and after the reaction (for example, the increase of Z isomer's proportion after the reaction than before the reaction).

In the present description, hydrohalofluoroolefin means an unsaturated hydrocarbon compound that contains in the molecule at least one hydrogen atom, at least one fluorine atom, and at least one carbon-carbon double bond, and it may contain chlorine atom, bromine atom or iodine atom as a halogen atom other than fluorine atom. That is, this hydrohalofluoroolefin also contains a compound that is generally called hydrofluoroolefin.

In the present description, hydrohalofluoroolefin isomer (isomer 1) is the starting material according to the method of the present invention and means a hydrohalofluoroolefin of E isomer or Z isomer.

Hydrohalofluoroolefin isomer (isomer 1) is the product according to the method of the present invention. It means a hydrohalofluoroolefin of Z isomer when the isomer 1 is E isomer, and it means a hydrohalofluoroolefin of E isomer when the isomer 1 is Z isomer.

In the present description, "metal fluorinated compound" refers to a compound having at least a bond between metal and fluorine atom, and may also contain another non-metal atom.

Advantageous Effect of the Invention

According to the present invention, it is possible to provide a method for suppressing lowering of catalyst performance in a method for efficiently isomerizing a hydrohalofluoroolefin isomer (isomer 1) to produce the corresponding hydrohalofluoroolefin isomer (isomer 2).

MODE FOR IMPLEMENTING THE INVENTION

In the following, the present invention is described in detail, but is not interpreted as being limited to the description of the following embodiments and examples.

The present invention provides a method in which a composition containing at least a predetermined hydrohalofluoroolefin isomer (isomer 1) is contacted with a catalyst in a gas phase to suppress performance lowering of the catalyst, thereby efficiently producing the corresponding hydrohalofluoroolefin isomer (isomer 2).

(Method for Producing Hydrohalofluoroolefin Isomer (Isomer 2))

A method of the present invention for isomerizing a hydrohalofluoroolefin isomer (isomer 1) to produce the corresponding hydrohalofluoroolefin isomer (isomer 2) contains at least the following step 1:

step 1 of contacting a composition that contains at least a hydrohalofluoroolefin isomer (isomer 1) and that has been adjusted to 100 ppm or lower in moisture concentration, with a catalyst in a gas phase, thereby obtaining a product.

[Hydrohalofluoroolefin Isomer (Isomer 1)]

The hydrohalofluoroolefin isomer (isomer 1) according to the method of the present invention is preferably a hydrohalofluoroolefin having two to six carbon atoms. In particular, the method of the present invention is preferable for isomerizing hydrohalofluoroolefins having three to six carbon atoms, that is, hydrohalofluoropropene, hydrohalofluorobutene, hydrohalofluoropentene, and hydrohalofluorohexene. It is particularly preferable for isomerizing hydrohalofluoropropene.

A preferable hydrohalofluoroolefin isomer (isomer 1), which is isomerized by the method of the present invention, may be one containing 1 to 11 fluorine atoms, 0 to 3 halogen atoms selected from Cl and Br, and a hydrogen atom(s) as the remainder (hydrohalofluoroolefin isomer (isomer 1) contains at least one hydrogen atom). In particular, the hydrohalofluoropropene is preferably one having 1 to 5 fluorine atoms, 1 to 5 atoms selected from H, Cl and Br, and at least one H, and is particularly preferably one having 3 to 5 fluorine atoms, 1 to 3 atoms selected from H, Cl and Br, and at least one H. The hydrohalofluorobutene is preferably one having 1 to 7 fluorine atoms, 1 to 7 atoms selected from H, Cl and Br, and at least one H, and is particularly preferably one having 5 to 7 fluorine atoms, 1 to 3 atoms selected from H, Cl and Br, and at least one H. The hydrohalofluoropentene is preferably one having 1 to 9 fluorine atoms, 1 to 9 atoms selected from H, Cl and Br, and at least one H, and is particularly preferably one having 7 to 9 fluorine atoms, 1 to 3 atoms selected from H, Cl and Br, and at least one H. The hydrohalofluorohexene is preferably one having 1 to 11 fluorine atoms, 1 to 11 atoms selected from H, Cl and Br, and at least one H, and is particularly preferably one having 9 to 11 fluorine atoms, 1 to 3 atoms selected from H, Cl and Br, and at least one H.

Therefore, a preferable group of a preferable hydrohalofluoropropene to be isomerized by the method of the present invention can be represented by the following general formula (1).

$$(CX^1X^2X^3)CX^4=CX^5X^6 \tag{1}$$

In the general formula (1), each of $X^1$ to $X^6$ is independently H, F, Cl or Br, and, of $X^1$ to $X^6$, one to five of them are F, the rest is H, Cl or Br, and at least one of them is H.

A hydrohalofluoropropene to be isomerized by the method of the present invention may be a hydrohalofluoropropene represented by the following general formula (2).

$$(CFX^2X^3)CX^4=CX^5X^6 \tag{2}$$

In the general formula (2), each of $X^2$ to $X^6$ is independently H, F, Cl or Br, and, of $X^2$ to $X^6$, at least one of them is F, and at least one of them is H.

As the particularly preferable hydrohalofluoropropene, it is possible to cite a trifluoropropene selected from 1-chloro-3,3,3-trifluoropropene ($CF_3CH=CHCl$) and 1,2-dichloro-3,3,3-trifluoropropene ($CF_3CCl=CHCl$), a tetrafluoropropene selected from 1,3,3,3-tetrafluoropropene ($CF_3CH=CHF$), 1-chloro-1,3,3,3-tetrafluoropropene ($CF_3CH=CClF$), 2-chloro-1,3,3,3-tetrafluoropropene ($CF_3CCl=CHF$) and 1-chloro-2,3,3,3-tetrafluoropropene ($CF_3CF=CHCl$), and a pentafluoropropene selected from 1,2,3,3,3-pentafluoropropene ($CF_3CF=CHF$).

As a more preferable hydrohalofluoropropene, it is possible to cite a hydrohalofluoropropene represented by the following general formula (3), that is, 1-chloro-3,3,3-trifluoropropene ($CF_3CH=CHCl$) and 1,3,3,3-tetrafluoropropene ($CF_3CH=CHF$).

$$CF_3CH=CHX^7 \tag{3}$$

In the general formula (3), $X^7$ is F or Cl.

A composition containing at least a hydrohalofluoroolefin isomer (isomer 1) according to the present invention (hereinafter it may be referred to as "composition according to the present invention") contains a hydrohalofluoroolefin isomer (isomer 1) by 5 mass % or greater, preferably 30 weight % or greater, more preferably as a main component. Herein, containing a hydrohalofluoroolefin isomer (isomer 1) as a main component refers to containing in the composition a hydrohalofluoroolefin isomer (isomer 1) by 50 mass % or greater, preferably 70 mass % or greater, more preferably 90 mass % or greater. Furthermore, it is particularly preferable that the composition according to the present invention consists essentially of a hydrohalofluoroolefin isomer (isomer 1). Herein, consisting essentially of a hydrohalofluoroolefin isomer (isomer 1) means that a hydrohalofluoroolefin isomer (isomer 1) is contained in the composition according to the present invention by 95 mass % or greater.

Besides a hydrohalofluoroolefin isomer (isomer 1), the composition according to the present invention may contain the corresponding hydrohalofluoroolefin isomer (isomer 2). The hydrohalofluoroolefin isomer (isomer 2) is the target material, and its content is not particularly limited. The composition according to the present invention may contain other components other than a hydrohalofluoroolefin isomer (isomer 1) and the corresponding hydrohalofluoroolefin isomer (isomer 2). Herein, the types of "other components" are not particularly limited, but may be various components. They may be either a single type or a plurality of types. As specific examples of "other components", it is possible to cite hydrohalofluorocarbons or hydrofluorocarbons, obtained by fluorinating hydrohalofluoroolefins, but they are not limited to these. In case that "other components" are contained, their contents are preferably 10 mass % or less, more preferably 5 mass % or less, particularly preferably 1 mass % or less, relative to the hydrohalofluoroolefin isomer (isomer 1).

As the composition containing at least a hydrohalofluoroolefin isomer (isomer 1) according to the present invention, there is used one having a moisture concentration of 100 ppm or less, preferably one of 70 ppm or less, particularly preferably one of 50 ppm or less, more preferably 30 ppm or less. The lower limit of moisture concentration is not particularly limited. That is, moisture concentration of the composition containing at least a hydrohalofluoroolefin isomer (isomer 1) may be 0-100 ppm, preferably 0-70 ppm, particularly preferably 0-50 ppm, more preferably 0-30 ppm.

Herein, moisture concentration (moisture content) of the composition according to the present invention can be measured by a Karl Fisher moisture meter. In case that the sample is a high-boiling-point substance, it is preferable that a given quantity of the liquid sample is taken into a syringe and then introduced as it is into a titration liquid of the Karl Fisher moisture meter to conduct the measurement. In case that the sample is a low-boiling-point substance, the liquid sample may vaporize. Therefore, it is preferable to conduct the measurement with a specification that allows the sample to be introduced as it is even if it evaporates on the way by previously connecting the sample container and an introducing section of the moisture meter through a tube. Furthermore, it is also possible to conduct the measurement by introducing the sample, using a commercial vaporization device.

A hydrohalofluoroolefin isomer (isomer 1) according to the present invention may be Z isomer or E isomer. Furthermore, besides a hydrohalofluoroolefin isomer (isomer 1) according to the present invention, the corresponding hydrohalofluoroolefin isomer (isomer 2) may be contained as other components in the composition according to the present invention. It may contain hydrohalofluorocarbons or hydrofluorocarbons, obtained by fluorinating hydrohalofluoroolefins.

In order to adjust moisture concentration of the composition according to the present invention to 100 ppm or less, preferably 70 ppm or less, particularly preferably 50 ppm or less, more preferably 30 ppm or less, it is optional to conduct a dehydration treatment on the composition according to the present invention to reduce the moisture concentration.

The method of this dehydration treatment is not particularly limited. For example, a method by distillation or a method using a dehydrating agent can be applied. By performing distillation, it is possible to conduct a dehydration treatment on the composition according to the present invention, and it is also possible to increase the content of the hydrohalofluoroolefin isomer (isomer 1) in the composition according to the present invention.

In this method using a dehydrating agent, the composition according to the present invention is contacted with a dehydrating agent to reduce its moisture concentration. The type of this dehydrating agent is not particularly limited. For example, zeolite, molecular sieve, allophane, etc. can be cited. As to zeolite shape, it is possible to use one having powder shape, granular shape, pellet shape, spherical shape, rod shape, etc., and one resulting from forming and baking and having a spherical shape or rod shape is easy in handling and preferable. Furthermore, pore size of zeolite and molecular sieve is not particularly limited, but it is possible to use zeolite and molecular sieve of various pore sizes. In particular, around 2.0 to 6.0 angstroms is preferable, since it is easy to selectively separate moisture from the composition according to the present invention. A method for contacting the composition according to the present invention and a dehydrating agent is not particularly limited. It may be a contact by standstill between the composition according to the present invention and a dehydrating agent. It is efficient and preferable to allow the composition according to the present invention in a gaseous or liquid condition to flow through a container filled with a dehydrating agent to make a contact with the dehydrating agent. Since allophane has both of dehydration ability and deacidification ability, it is possible to conduct deacidification by the flow in a gaseous or liquid condition without going through the step of water washing. In the deacidification method using allophane, construction and operation of a dry process in which water is not brought into contact are possible. It is possible to use allophane in a shape of powder, grains, granules, pellets, etc. As an example of commercial products, it is possible to cite Secard made by Shinagawa Chemicals Co., Ltd.

Furthermore, as a method of dehydration treatment of the composition according to the present invention, it is optional to use both of a method by distillation and a method by a dehydrating agent due to showing a higher dehydration performance. It is preferable to adopt a method in which the composition according to the present invention is subjected to distillation and is contacted with the above-mentioned dehydrating agent before and/or after the distillation. With this, it is possible to adjust moisture concentration of the composition according to the present invention to a lower level. Depending on the type of hydrohalofluoroolefin isomer (isomer 1), it may form an azeotropic composition or azeotrope-like composition with water (for example, E-1,3,3-tetrafluoropropene (see JP Patent Application Publication 2013-525486), E-1-chloro-3,3,3-trifluoropropene (JP Patent Application Publication 2012-506944), etc.). Therefore, as a method of dehydration treatment of the composition according to the present invention, it is particularly preferable to adopt a method in which the composition according to the present invention is subjected to distillation and is contacted with a dehydrating agent, at least prior to the distillation. It is more preferable to adopt a method of conducting a further contact with a dehydrating agent after the distillation.

The composition according to the present invention adjusted to having a desired moisture concentration is then supplied to an isomerization reaction system. If it is possible to confirm that the composition according to the present invention has a predetermined moisture concentration, it is not always necessary to conduct the above-mentioned dehydration treatment, but it can be supplied to the isomerization reaction system as it is. Such mode is also naturally contained as one mode of the present invention.

As to the reaction manner of isomerization according to the present invention, it is possible to adopt either a gas-phase reaction or a liquid-phase reaction. Furthermore, the treatment manner may be flow type, half batch type or batch type. It is possible to suitably adopt a manner by combining these reaction manner and treatment manner. In case that a chemical substance involved in the reaction is low in boiling point, a gas-phase flow type is practically the most preferable. In a gas-phase flow type, the catalyst holding method may be conducted by any type such as fixed bed, fluidized bed, moving bed, etc. Conducting by fixed bed is easy and therefore preferable.

[Catalyst]

As a catalyst used in the present invention, it suffices to use one that is capable of isomerizing a hydrohalofluoroolefin isomer (isomer 1) in the composition according to the present invention by contacting the composition according to the present invention with the catalyst in a gas phase. The catalyst may be a non-supported catalyst or supported catalyst.

As a non-supported catalyst, a metal compound, such as a metal oxide and a metal fluorinated compound that has been partially or totally fluorinated, is preferable. The type of metal contained in these metal compounds is not particularly limited. For example, it is possible to cite at least one metal selected from the group consisting of aluminum, chromium, titanium, manganese, iron, nickel, cobalt, copper, magnesium, zirconium, molybdenum, zinc, tin, lanthanum, niobium, tantalum, and antimony. In particular, at least one metal selected from the group consisting of aluminum, chromium, manganese, zirconium, titanium, and magnesium is preferable. The metal may be single or a composite metal containing at least two metals.

The material for preparing the metal fluorinated compound is not particularly limited. For example, it is optional to use a metal oxide, etc. The type of this metal oxide is not particularly limited. For example, it is possible to cite an oxide of at least one metal selected from the group consisting of aluminum, chromium, titanium, manganese, iron, nickel, cobalt, copper, magnesium, zirconium, molybdenum, zinc, tin, lanthanum, niobium, tantalum, and antimony. In particular, an oxide of at least one metal selected from the group consisting of aluminum, chromium, manganese, zirconium, titanium, and magnesium is preferable. Metal contained in the metal oxide may be single, and it may be used as an oxide of a composite metal containing at least two metals. The metal fluorinated compounds can be obtained by conducting a fluorination treatment on these metal oxides, etc. Some metal oxides used as materials for obtaining the metal fluorinated compounds exist as having different crystal systems, but any of them can be used.

The composite metal is preferably one that contains as a main component at least one metal selected from the group consisting of aluminum, chromium, manganese, zirconium, titanium and magnesium and that contains as a minor component at least one metal selected from the group consisting of aluminum, chromium, titanium, manganese, iron, nickel, copper, cobalt, magnesium, zirconium, molybdenum, zinc, tin, lanthanum, niobium, tantalum, and antimony.

As an oxide of such composite metal, it is possible to cite a composite material that is a combination of, for example, alumina and chromia, alumina and zirconia, alumina and titania, or alumina and magnesia. Each combination is particularly preferably one containing 50 atomic percent or more, more preferably 80 atomic percent or more, of aluminum. If it is 50 atomic percent or more, it is possible to make the isomerization reaction progress with a good conversion rate.

A metal oxide used as a material of the metal fluorinated compound may take more than one crystal form. For example, alumina has γ-alumina and α-alumina, and titania has anatase and rutile crystal forms. Either crystal form will do, but, in alumina, γ-alumina is preferable due to its large surface area.

The method for preparing the metal fluorinated compound is not particularly limited. It may be conducted by contacting a fluorination agent, such as hydrogen fluoride, fluorinated hydrocarbon, or fluorochlorinated hydrocarbon, with the above-mentioned metal oxide or composite metal oxide. Normally, it is preferable to stepwisely conduct this fluorination treatment. The fluorination treatment using hydrogen fluoride is accompanied by a large heat generation. Therefore, it is preferable to fluorinate the metal oxide (composite metal oxide) firstly by a diluted hydrogen fluoride gas at a relatively low temperature, followed by conducting the same with a gradual increase of concentration and/or temperature. At the final stage, it is preferable to conduct the same at a temperature that is the reaction temperature of the isomerization or higher. Besides this condition, in order to make the reaction progress stably, it is preferable that the fluorination treatment temperature is 200° C. or higher and that the fluorination treatment is conducted by hydrogen fluoride at 400° C. or higher, more preferably 500° C. or higher. There is no particular upper limit in the temperature, but exceeding 900° C. is difficult in terms of heat resistance of the fluorination treatment apparatus. Practically, it is preferable to conduct that at 600° C. or lower. As mentioned above, in order to make the reaction progress stably, it is preferable to use as the catalyst a metal fluorinated compound prepared by previously conducting the fluorination treatment on a metal oxide (composite metal oxide) with a fluorination agent, such as hydrogen fluoride, a fluorinated hydrocarbon or a fluorochlorinated hydrocarbon, at a temperature that is a predetermined reaction temperature or higher, prior to its use.

The catalyst used in the present invention, such as metal oxide or metal fluorinated compound, is preferably subjected, upon its use, to a fluorination treatment by a fluorination agent. This fluorination treatment can be conducted in accordance with the above-mentioned example of the metal fluorinated compound preparation method.

As the catalyst according to the present invention, it is optional to use a supported catalyst that supports a metal compound. As the support of this supported catalyst, it is optional to use carbon or the metal (including the composite metal) mentioned above as the non-supported catalyst. The metal used as the support may be either the metal oxide or metal fluorinated compound, which is mentioned above as the non-supported catalyst. Specifically, it is optional to singly use as the support an oxide of at least one metal selected from the group consisting of aluminum, chromium, titanium, manganese, iron, nickel, cobalt, copper, magnesium, zirconium, molybdenum, zinc, tin, lanthanum, niobium, tantalum, and antimony, preferably an oxide of at least one metal selected from the group consisting of aluminum, chromium, manganese, zirconium, titanium, and magnesium. Alternatively, it is optional to use as the support an oxide of the composite metal or a fluorinated compound prepared by a partial or total fluorination of the same. The oxide of the composite metal is preferably an oxide that contains, for example, as a main component at least one metal selected from the group consisting of aluminum, chromium, manganese, zirconium, titanium and magnesium and that contains as a minor component at least one metal selected from the group consisting of aluminum, chromium, titanium, manganese, iron, nickel, copper, cobalt, magnesium, zirconium, molybdenum, zinc, tin, lanthanum, niobium, tantalum, and antimony.

As the metal contained in the metal compound to be supported, it is possible to cite aluminum, chromium, titanium, manganese, iron, nickel, cobalt, copper, magnesium, zirconium, molybdenum, zinc, tin, lanthanum, niobium, tantalum, antimony, etc. Of these, aluminum, chromium, titanium, iron, nickel, cobalt, copper, zirconium, zinc, tin, lanthanum, niobium, tantalum, and antimony are preferable. These metals are supported as fluorides, chlorides, fluorochlorides, oxyfluorides, oxychlorides, oxyfluorochlorides, etc. The metal compounds may be singly supported, or at least two of them may be supported together.

Specifically, as the metal compound to be supported, it is possible to use chromium nitrate, chromium trichloride, potassium dichromate, titanium trichloride, manganese nitrate, manganese chloride, ferric chloride, nickel nitrate, nickel chloride, cobalt nitrate, cobalt chloride, antimony pentachloride, magnesium chloride, magnesium nitrate, zirconium chloride, zirconium oxychloride, zirconium nitrate, copper(II) chloride, zinc(II) chloride, lanthanum nitrate, tin tetrachloride, etc., but it is not limited to these.

In order to make the reaction progress stably, the catalyst prepared by supporting the above-mentioned metal compound on the support may be subjected to a fluorination treatment prior to its use, and doing so is preferable. That is, the catalyst according to the present invention may be a catalyst prepared by conducting a fluorination treatment on a supported catalyst that supports a metal compound on a support. In this case, prior to its use, it is preferable to previously conduct a treatment with a fluorination agent, such as hydrogen fluoride, a fluorinated hydrocarbon or fluorochlorinated hydrocarbon, at a temperature that is a predetermined reaction temperature or higher, by a method similar to that of the above-mentioned metal oxide fluorination treatment.

Herein, in case that a layer of a metal compound as the supported material entirely covers the support that is a metal oxide, the supported material is mainly subjected to the fluorination treatment than the support. As a result, the supported material mainly acts as a catalyst of the isomerization reaction. In case that a layer of a metal compound as the supported material does not entirely covers the support that is a metal oxide, the support, together with the supported material, is also subjected to the fluorination treatment in the fluorination treatment step. As a result, the support, together with the supported material, may also act as a catalyst in the isomerization reaction. Thus, in case that the support, together with the supported material, acts as a catalyst, it may act as a composite metal fluorinated compound, similar to a non-supported catalyst, not as a supported catalyst.

As preferable examples of a catalyst of the isomerization reaction according to the present invention, it is possible to cite fluorinated alumina, fluorinated zirconia, fluorinated chromia, and chromium-supported activated carbon, particularly preferably fluorinated alumina, fluorinated zirconia and fluorinated chromia. It is preferable that these catalysts are previously subjected to the fluorination treatment, prior to the reaction.

The percentage of metal by mass relative to the total mass of the catalyst including the support and the supported material is 0.1 to 80 mass %, preferably 1 to 50 mass %. If it is 0.1 mass % or greater, a good catalytic effect can be obtained. If it is 80 mass % or less, a stable supporting is possible. In case that the supported material is a solid metal salt, the percentage of the metal by mass relative to the total mass of the catalyst is 0.1 to 40 mass %, preferably 1 to 30 mass %.

[Contact Temperature (Reaction Temperature)]

The contact temperature (reaction temperature) in the isomerization reaction may be 0 to 600° C., preferably 20 to 550° C., particularly preferably 50 to 500° C., although the lower limit temperature depends on properties (boiling point, etc.) of the reaction raw material. In case that the contact temperature exceeds 600° C., the hydrohalofluoroolefin isomer (isomer 1) and/or the hydrohalofluoroolefin isomer (isomer 2) as the target material may decompose on the catalyst and/or may cause coking. Setting the contact temperature unnecessarily high is waste of energy and increases load on the apparatus. The contact temperature that is lower than 0° C. is not practical from the viewpoint of handling in the reaction operation.

The contact temperature and the contact time, during which the composition according to the present invention is contacted with the catalyst, are in a trade-off relation. A short contact time if the contact temperature is high and a long contact time if the contact temperature is low are more preferable in terms of efficiency of the isomerization of the hydrohalofluoroolefin isomer (isomer 1) in the composition according to the present invention.

[Contact Time]

In the present description, contact time of the reaction according to the present invention is defined as follows. That is, contact time is represented by the value (seconds) obtained by dividing volume A (mL) of the catalyst by the raw material supply rate B (mL/s). The value of B represents the volume of the raw material gas introduced into the reaction vessel per second. In this case, the raw material gas is considered as being ideal gas, and the value of B is calculated from the number of moles, pressure and temperature of the raw material gas. In the reaction vessel, by-production of other compounds other than the raw material and the target material and/or the change of the number of moles may occur, but is not considered when calculating the contact time.

The contact time is determined depending on the reaction raw material, the reaction vessel's temperature (contact temperature) and/or shape, and the catalyst type, which are used in the present invention. Therefore, it is desirable to optimize the contact time by suitably adjusting the supply rate of the reaction raw material for each of the reaction raw material, the reaction apparatus preset temperature, the reaction vessel shape, and the catalyst type. Since the proportion of each isomer is controlled by a thermodynamic equilibrium, conversion is roughly determined. Normally, it is preferable to adopt a contact time such that a raw material conversion of 10% or greater can be obtained, from the viewpoint of recovery and reuse of the unreacted raw material. Furthermore, it is preferable to optimize the contact time to obtain a conversion of 15% or greater.

The optimum contact time in the present invention is 0.01 to 500 seconds, preferably 0.1 to 250 seconds, more preferably 1 to 150 seconds. In general, if the contact time is shorter than these, there may be shown only a conversion that is largely deviated from the thermodynamic equilibrium composition. In contrast, if it is longer than these, productivity may become worse and/or turning into tar may occur, although showing a conversion close to the equilibrium composition. The above-mentioned contact time may be suitably changed in accordance with the reaction pressure.

In the isomerization reaction according to the present invention, an appropriate combination of the contact temperature (reaction temperature) and the contact time is an important element. If the reaction temperature is 0 to 600° C., 0.01 to 500 seconds is preferable in contact time. If 20 to 550° C., 0.1 to 250 seconds is preferable. If 50 to 500° C., 1 to 150 seconds is preferable. In particular, from the viewpoint of efficiently producing the target material by reducing the formation of by-products, it is more preferable that the contact time is short if the reaction temperature is high and that the contact time is long if the reaction temperature is low.

[Others, Reaction Pressure, Etc.]

In the isomerization reaction according to the present invention, the reaction pressure is not particularly limited, but operation at around ordinary pressure is easy. The reaction under a pressure of 1 MPa or higher not only requires a high-price, pressure-proof apparatus, but also causes a risk of polymerization of the raw material or the product. The method for heating the apparatus is not particularly limited, but it is preferable to take a direct heating method with an electric heater or burner, or an indirect heating method using molten salt, sand, etc.

The product resulting from the isomerization reaction contains at least a hydrohalofluoroolefin isomer (isomer 2) as the target material. It is preferable to separate this hydrohalofluoroolefin isomer (isomer 2) from the product resulting from the isomerization reaction. The method for separating the hydrohalofluoroolefin isomer (isomer 2) from the product resulting from the isomerization reaction is not particularly limited. It is possible to separate the hydrohalofluoroolefin isomer (isomer 2) from the product resulting from the isomerization reaction, for example, by distillation.

Furthermore, the product resulting from the isomerization reaction may contain acid component that is used or possible to be formed in the process of the catalyst fluorination treatment and/or the isomerization reaction, besides the hydrohalofluoroolefin isomer (isomer 2) as the target material. It is preferable to remove this acid component from the product, prior to the separation of the hydrohalofluoroolefin isomer (isomer 2) from the product resulting from the isomerization reaction, in order to prevent accumulation of impurities of the product and to reduce the damage against the apparatus and the facility.

The method for removing acid component from the product resulting from the isomerization reaction is not particularly limited. For example, it is optional to remove the acid component from the product by conducting a washing treatment using water, etc. Furthermore, it is optional to conduct a dehydration treatment on the product resulting from the isomerization reaction to remove moisture. It is optional to adopt a combination of this and the acid component removal method. This dehydration method is not particularly limited. For example, a method by distillation or a method by a dehydrating agent can be applied, a combination of these methods may be used, and it may be conducted two times or more. In terms of efficiency, a method by a dehydrating agent is preferable. In a method by a dehydrating agent, the product resulting from the isomerization and a dehydrating agent are contacted together. The type of this dehydrating agent is not particularly limited. It is possible to cite, for example, zeolite, molecular sieve, allophane, etc. As to zeolite shape, it is possible to use one having powder shape, granular shape, pellet shape, spherical shape, rod shape, etc., and one resulting from forming and baking and having a spherical shape or rod shape is easy in handling and preferable. Furthermore, pore size of zeolite and molecular sieve is not particularly limited, but around 2.0 to 6.0 angstroms is preferable. A method for contacting the composition containing hydrohalofluoroolefin isomer (isomer 2) with a dehydrating agent is not particularly limited. Normally, it is efficient and preferable to allow the composition containing at least hydrohalofluoroolefin isomer (isomer 2), which is in a gaseous or liquid condition, to flow through a container filled with a dehydrating agent. Since allophane has both of dehydration ability and deacidification ability, it is possible to conduct deacidification by the flow in a gaseous or liquid condition without going through the step of water washing. In the deacidification method using allophane, construction and operation of a dry process in which water is not brought into contact are possible. It is possible to use allophane in a shape of powder, grains, granules, pellets, etc. As an example of commercial products, it is possible to cite Secard made by Shinagawa Chemicals Co., Ltd. In order that moisture concentration of the composition containing at least hydrohalofluoroolefin isomer (isomer 2) may be adjusted even low, it is particularly preferable to adopt a method in which the composition according to the present invention is subjected to distillation and is contacted with a dehydrating agent, at least prior to the distillation. It is more preferable to adopt a method of conducting a further contact with a dehydrating agent after the distillation. In distillation in this dehydration treatment, it is optional to conduct a separation of hydrohalofluoroolefin isomer (isomer 2) from the product resulting from the isomerization, as well as conducting the removal of moisture.

These methods of removing acid component and removing moisture may each be repeated or conducted stepwise. It is preferable to eventually remove acid component and moisture, which can be contained in the composition containing at least hydrohalofluoroolefin isomer (isomer 2). It suffices that the raw material composition containing hydrohalofluoroolefin isomer (isomer 2), which has been separated and recovered, has a desired moisture concentration.

Based on these post-treatment methods after the reaction, the method of the present invention may further contain the following step 2:

step 2 of removing acid component from the product obtained by step 1 and then separating hydrohalofluoroolefin isomer (isomer 2) from the product from which the acid component has been removed.

The product resulting from the isomerization reaction may contain hydrohalofluoroolefin isomer (isomer 1). This hydrohalofluoroolefin isomer (isomer 1) may be separated from the product resulting from the isomerization and then reused as the raw material of the isomerization according to the present invention. Even in this case, acid component that is used or possible to be formed in the process of the catalyst fluorination treatment and/or the isomerization reaction may be contained. It is preferable to remove this acid component from the product and then reuse hydrohalofluoroolefin isomer (isomer 2) in order to prevent accumulation of impurities of the product and to reduce the damage against the apparatus and the facility.

The method for removing acid component from the product resulting from the isomerization reaction is not particularly limited. For example, it is optional to remove the acid component from the product by conducting a washing treatment using water, etc. Furthermore, it is optional to conduct a dehydration treatment on the product resulting from the isomerization reaction to remove moisture. It is optional to adopt a combination of this and the acid component removal method. This dehydration method is not particularly limited. For example, it is possible to adopt a method similar to the above-mentioned dehydration treatment method, and it is preferable to adopt this method. Furthermore, these methods of removing acid component and removing moisture may each be repeated or conducted stepwise. It is preferable to eventually remove acid component and moisture, which can be contained in hydrohalofluoroolefin isomer (isomer 1).

Hydrohalofluoroolefin isomer (isomer 1) that is reused as the raw material of the isomerization reaction according to the present invention may coexist with other components. That is, this hydrohalofluoroolefin isomer (isomer 1) may be a composition containing at least hydrohalofluoroolefin isomer (isomer 1). The composition containing at least hydrohalofluoroolefin isomer (isomer 1) mentioned herein may have the same meaning as that of the above-mentioned composition according to the present invention. This composition containing at least hydrohalofluoroolefin isomer (isomer 1) may be adjusted to a predetermined moisture concentration at this stage. Alternatively, the adjustment may be conducted after step 1.

Based on such method for reusing hydrohalofluoroolefin isomer (isomer 1), the method of the present invention may further contain the following step 3 and step 4:

step 3 of removing acid component from the product obtained by step 1 and then separating a composition containing at least hydrohalofluoroolefin isomer (isomer 1) from the product from which the acid component has been removed; and step 4 of reusing the composition containing at least hydrohalofluoroolefin isomer (isomer 1), which has been separated by step 3, as a composition containing at least hydrohalofluoroolefin isomer (isomer 1) of step 1.

[Catalyst Activation]

It is possible to suppress the catalyst performance lowering by adopting the production method of the present invention, but the catalyst performance may lower by a chronological factor, etc. In such case, it is possible to efficiently produce hydrohalofluoroolefin isomer (isomer 2) by activating the catalyst. Normally, the catalyst with a lowered performance can be activated by baking under high temperature. If the performance lowering is assumed to be caused mainly by the effect of moisture, it is efficient and preferable to bake the catalyst at high temperature by gas flow. It is particularly preferable to adopt this catalyst activation method in the method according to the present invention. The gas upon baking is not limited, but it is preferable to conduct that under inert gas. It is particularly preferable to conduct that under nitrogen. It is preferable that the baking temperature is higher than the isomerization reaction temperature, but it may be conducted at 0° C. or higher, preferably 200° C. or higher, particularly preferably 400° C. or higher, more preferably 500° C. or higher. Furthermore, if the performance lowering is assumed to be caused by coking, it is possible to remove the coking material by conducting an air baking at high temperature. It is preferable that the baking temperature in this case also is higher than the isomerization reaction temperature, but it may be conducted at 0° C. or higher, preferably 200° C. or higher, particularly preferably 400° C. or higher, more preferably 500° C. or higher. If there is a risk of affecting the reaction, such as behavior change over time during the reaction, as a result of lowering of the degree of fluorination of the catalyst by the air baking, it is possible to stably conduct the isomerization reaction again by subsequently fluorinating the catalyst by a fluorination agent. It is preferable that the catalyst fluorination treatment is conducted at a temperature that is the reaction temperature of the isomerization reaction or higher. It may be conducted at 0° C. or higher, preferably 200° C. or higher, particularly preferably 400° C. or higher, more preferably 500° C. or higher. The upper limit of the temperature is not particularly limited. If it exceeds 900° C., it is difficult in terms of heat resistance of the fluorination treatment apparatus. Practically, it is preferable to conduct that at 600° C. or lower, while setting each of the above-mentioned temperatures as the lower limit.

(Isomerization of Hydrohalofluoropropene Isomer (Isomer 1) Represented by the General Formula (3))

There is explained a method for isomerizing a hydrohalofluoropropene isomer (isomer 1) represented by the general formula (3) to produce the corresponding hydrohalofluoropropene isomer (isomer 2) represented by the general formula (3).

A composition that contains at least a hydrohalofluoropropene isomer (isomer 1) represented by the general formula (3) and that has a moisture concentration secured to be 100 ppm or lower, preferably 70 ppm or lower, particularly preferably 50 ppm or lower, more preferably 30 ppm or lower, is contacted with a catalyst in a gas phase to isomerize the hydrohalofluoropropene isomer (isomer 1), thereby producing the corresponding hydrohalofluoropropene isomer (isomer 2). By using a composition that contains at least a hydrohalofluoropropene isomer (isomer 1) represented by the general formula (3) and that has been adjusted to a predetermined moisture concentration, it is possible to suppress the catalyst performance lowering, thereby efficiently producing the corresponding hydrohalofluoropropene isomer (isomer 2).

The hydrohalofluoropropene isomer (isomer 1) represented by the general formula (3) may be either of E-1,3,3,3-tetrafluoropropene, Z-1,3,3,3-tetrafluoropropene, E-1-chloro-3,3,3-trifluoropropene, and Z-1-chloro-3,3,3-trifluoropropene. The corresponding hydrohalofluoropropene isomer (isomer 2) represented by the general formula (3) means Z-1,3,3,3-tetrafluoropropene in case that the hydrohalofluoropropene isomer (isomer 1) is E-1,3,3,3-tetrafluoropropene, means E-1,3,3,3-tetrafluoropropene in case that the isomer 1 is Z-1,3,3,3-tetrafluoropropene, means Z-1-chloro-3,3,3-trifluoropropene in case that the isomer 1 is E-1-chloro-3,3,3-trifluoropropene, and means E-1-chloro-3,3,3-trifluoropropene in case that the isomer 1 is Z-1-chloro-3,3,3-trifluoropropene. In the case of conducting the isomerization at low temperatures, isomerization of Z isomer of the hydrohalofluoropropene isomer (isomer 1) represented by the general formula (3) will work dominantly by a thermodynamic equilibrium. In the case of conducting that at high temperatures, isomerization of E isomer of the hydrohalofluoropropene isomer (isomer 1)

represented by the general formula (3) is preferable if considered from a similar viewpoint.

The composition containing at least hydrohalofluoroolefin isomer (isomer 1) represented by the general formula (3) contains at least hydrohalofluoroolefin isomer (isomer 1) represented by general formula (3) by 5 mass % or greater, preferably 30 mass % or greater. More preferably, it contains hydrohalofluoroolefin isomer (isomer 1) as a main component. Herein, containing a hydrohalofluoroolefin isomer (isomer 1) represented by the general formula (3) as a main component refers to containing in the composition a hydrohalofluoroolefin isomer (isomer 1) represented by the general formula (3) by 50 mass % or greater, preferably 70 mass % or greater, more preferably 90 mass % or greater. Furthermore, it is particularly preferable that the composition containing at least a hydrohalofluoroolefin isomer (isomer 1) represented by the general formula (3) consists essentially of a hydrohalofluoroolefin isomer (isomer 1) represented by the general formula (3). Herein, consisting essentially of a hydrohalofluoroolefin isomer (isomer 1) represented by the general formula (3) means that a hydrohalofluoroolefin isomer (isomer 1) represented by the general formula (3) is contained in the composition by 95 mass % or greater.

Besides a hydrohalofluoroolefin isomer (isomer 1) represented by the general formula (3), the composition containing at least the hydrohalofluoroolefin isomer (isomer 1) represented by the general formula (3) may contain the corresponding hydrohalofluoroolefin isomer (isomer 2) represented by the general formula (3). The corresponding hydrohalofluoroolefin isomer (isomer 2) represented by the general formula (3) is the target material, and its content is not particularly limited. The composition containing at least a hydrohalofluoroolefin isomer (isomer 1) represented by the general formula (3) may contain other components other than the hydrohalofluoroolefin isomer (isomer 1) represented by the general formula (3) and the corresponding hydrohalofluoroolefin isomer (isomer 2) represented by the general formula (3). Herein, the types of "other components" are not particularly limited, but may be various components. They may be either a single type or a plurality of types. As specific examples of "other components", it is possible to cite hydrohalofluorocarbons or hydrofluorocarbons, obtained by fluorinating hydrohalofluoroolefins, but they are not limited to these. In case that "other components" are contained, their contents are preferably 10 mass % or less, more preferably 5 mass % or less, particularly preferably 1 mass % or less, relative to the hydrohalofluoroolefin isomer (isomer 1) represented by the general formula (3).

Besides a hydrohalofluoroolefin isomer (isomer 1) represented by the general formula (3), the composition containing at least the hydrohalofluoroolefin isomer (isomer 1) represented by the general formula (3) may contain other components. Herein, the types of other components are not particularly limited, but may be various components. They may be either a single type or a plurality of types. In case that other components are contained, their contents of the composition are 50 mass % or less, preferably 30 mass % or less, more preferably 10 mass % or less. Furthermore, it is particularly preferable that other components are substantially not contained in the composition. Herein, being substantially not contained means that other components are contained in the composition by 5 mass % or less. However, in case that other components are moisture, it is necessary that the composition containing at least a hydrohalofluoroolefin isomer (isomer 1) represented by the general formula (3) has a predetermined moisture concentration.

The method for isomerizing a hydrohalofluoropropene isomer (isomer 1) represented by the general formula (3) to produce the corresponding hydrohalofluoropropene isomer (isomer 2) can be explained in accordance with the above-mentioned method for isomerizing a hydrohalofluoroolefin isomer (isomer 1) to produce the corresponding hydrohalofluoroolefin isomer (isomer 2). That is, it can be explained by replacing hydrohalofluoroolefin isomer (isomer 1) with hydrohalofluoropropene isomer (isomer 1) represented by the general formula (3) and by replacing hydrohalofluoroolefin isomer (isomer 2) with hydrohalofluoropropene isomer (isomer 2) represented by the general formula (3).

The contact temperature (reaction temperature) in the isomerization reaction is also similar. In case that a hydrohalofluoropropene isomer (isomer 1) represented by the general formula (3) is E isomer (i.e., E-1,3,3,3-tetrafluoropropene or E-1-chloro-3,3,3-trifluoropropene), the contact temperature may be 150-600° C., preferably 200-550° C., particularly preferably 250-500° C. In this case, as suitably combined with the contact time, the contact time is preferably 0.01-500 seconds when the contact temperature is 150-600° C., is preferably 0.1-250 seconds when it is 200-550° C., and is preferably 1-150 seconds when it is 250-500° C. In particular, from the viewpoint of reducing the formation of by-products and efficiently producing the target material, it is more preferable that the contact time is short when the reaction temperature is high and that the contact time is long when the reaction temperature is low. Similarly, in case that a hydrohalofluoropropene isomer (isomer 1) represented by the general formula (3) is Z isomer (i.e., Z-1,3,3,3-tetrafluoropropene or Z-1-chloro-3,3,3-trifluoropropene), the contact temperature may be 40-500° C., preferably 45-400° C., particularly preferably 50-300° C. In this case, as suitably combined with the contact time, the contact time is preferably 5-400 seconds when the contact temperature is 40-500° C., is preferably 10-300 seconds when it is 45-400° C., and is preferably 15-200 seconds when it is 50-300° C. In particular, from the viewpoint of reducing the formation of by-products and efficiently producing the target material, it is more preferable that the contact time is short when the reaction temperature is high and that the contact time is long when the reaction temperature is low.

The above-mentioned reaction conditions are those assuming the operation at around ordinary pressure, but it is fully possible that the range of contact temperature and/or contact time varies in accordance with the reaction pressure.

EXAMPLES

In the following, GC % according to the compositional analysis value represents areal % of the composition obtained by measuring the reaction mixture by gas chromatography (detector: FID). The figure after the last digit shown was rounded thereto. For example, 0.01 GC % in Table 1 is referred to as being 0.005 areal % or greater and less than 0.015 areal %.

Preparation Example 1

A stainless steel (SUS 316L) reaction tube having a cylindrical shape (diameter: 2 cm; length: 40 cm) and equipped with an electric furnace was filled with 50 mL of a granular zirconia (made by Saint-Gobain Co., model number: SZ-31163), followed by increasing the temperature in the reaction tube until 200° C. while nitrogen gas was allowed to flow. At the point when water discharge from the reaction tube was not found, nitrogen gas was accompanied with hydrogen fluoride (HF), and its concentration was gradually increased. When hot spot resulting from fluorination of the loaded granular zirconia reached the exit end of the reaction tube, the temperature in the reaction tube was increased stepwise by 100° C. At the temperature at each step, it was maintained for one hour and then finally increased to 500° C. This condition was maintained for one hour. In this manner, a granular zirconia subjected to a fluorination treatment (hereinafter may be referred to as Catalyst 1) was prepared.

Preparation Example 2

A γ-alumina subjected to a fluorination treatment (hereinafter may be referred to as Catalyst 2) was prepared by a method similar to Preparation Example 1, except that it was filled with a γ-alumina (made by Sumica Alchem Co., Ltd.; model number: KHS-46) in place of the granular zirconia.

Example 1

By a pump, 20 kg of E-1,3,3,3-tetrafluoropropene in the form of liquid was delivered to and circulated through a drying tower filled with 200 g of ZEOLUM A-3 (made by Tosoh Corporation) as a dehydrating agent to conduct a dehydration treatment. As moisture concentration of E-1,3,3,3-tetrafluoropropene after the dehydration treatment was measured by a Karl Fisher moisture meter equipped with a vaporizer, it was less than 1 ppm. Herein, a moisture microanalyzer (made by Mitsubishi Chemical Analytech Co., Ltd., CA-200 type) was used as the Karl Fisher moisture meter. A liquefied gas vaporizer (made by the same company; model number: VG-200 type) was connected to the sample introducing section. The sample of a predetermined amount was vaporized and automatically injected to the moisture meter.

Then, 50 mL of Catalyst 1 prepared by Preparation Example 1 was loaded into a stainless steel (SUS 316L) reaction tube having a cylindrical shape (diameter: 2 cm; length: 40 cm) and equipped with an electric furnace. While nitrogen gas was allowed to flow at a flow rate of about 100 mL/minute, the temperature in the reaction tube was increased to 300° C.

Next, E-1,3,3,3-tetrafluoropropene (moisture concentration: less than 1 ppm) resulting from the above-mentioned dehydration treatment was previously vaporized, and its supply to the reaction tube was started at a rate calculated based on the time (15 seconds) of contact with the catalyst. When the flow rate of the organic matter became stable, the introduction of nitrogen gas was stopped.

The gas mixture discharged from the exit of the reaction tube was bubbled into water to remove an acid gas. Then, the obtained product was analyzed by gas chromatography. The results are shown in Table 1. In the table, 1234ze(E), 1234zc, 245fa and 1234ze(Z) respectively represent E-1,3,3,3-tetrafluoropropene, 1,1,3,3-tetrafluoropropene, 1,1,1,3,3-pentafluoropropane, and Z-1,3,3,3-tetrafluoropropene. The same shall apply in the following.

TABLE 1

| Moisture Concentration | Raw Material Composition (GC %) | | | |
|---|---|---|---|---|
| Less than 1 ppm | 1234ze(E) | 1234zc | 245fa | 1234ze(Z) |
|  | 99.97 | 0.00 | 0.01 | 0.01 |
| Raw Material Introduction | Reaction Product Composition (GC %) | | | |
| Integrated Amount (g) | 1234ze(E) | 1234zc | 245fa | 1234ze(Z) |
| 622 | 82.42 | 0.02 | 0.07 | 17.48 |
| 1,438 | 81.94 | 0.02 | 0.36 | 17.66 |

TABLE 1-continued

| 2,164 | 82.18 | 0.02 | 0.12 | 17.68 |
|---|---|---|---|---|
| 3,115 | 81.90 | 0.02 | 0.03 | 18.05 |
| 3,640 | 81.93 | 0.02 | 0.05 | 18.00 |
| 4,255 | 81.85 | 0.02 | 0.02 | 18.11 |
| 5,133 | 81.80 | 0.02 | 0.08 | 18.11 |

Example 2

The isomerization reaction was conducted similar to Example 1, except that the moisture-adjusted E-1,3,3,3-tetrafluoropropene (moisture concentration: 37 ppm) was used in place of the dehydrated E-1,3,3,3-tetrafluoropropene (moisture concentration: less than 1 ppm). The results are shown in Table 2.

TABLE 2

| Moisture Concentration | Raw Material Composition (GC %) | | | |
|---|---|---|---|---|
| 37 ppm | 1234ze(E) | 1234zc | 245fa | 1234ze(Z) |
|  | 99.97 | 0.00 | 0.01 | 0.02 |
| Raw Material Introduction | Reaction Product Composition (GC %) | | | |
| Integrated Amount (g) | 1234ze(E) | 1234zc | 245fa | 1234ze(Z) |
| 94 | 82.53 | 0.01 | 0.04 | 17.40 |
| 1,889 | 82.01 | 0.02 | 0.00 | 17.96 |
| 2,211 | 81.90 | 0.02 | 0.00 | 18.07 |
| 3,282 | 83.07 | 0.02 | 0.00 | 16.89 |
| 3,527 | 84.09 | 0.02 | 0.00 | 15.88 |
| 3,658 | 84.45 | 0.02 | 0.00 | 15.52 |
| 4,792 | 86.68 | 0.02 | 0.00 | 13.28 |
| 5,163 | 87.90 | 0.02 | 0.00 | 12.06 |

Example 3

The isomerization reaction was conducted similar to Example 1, except that the moisture-adjusted E-1,3,3,3-tetrafluoropropene (moisture concentration: 61 ppm) was used in place of the dehydrated E-1,3,3,3-tetrafluoropropene (moisture concentration: less than 1 ppm). The results are shown in Table 3.

TABLE 3

| Moisture Concentration | Raw Material Composition (GC %) | | | |
|---|---|---|---|---|
| 61 ppm | 1234ze(E) | 1234zc | 245fa | 1234ze(Z) |
|  | 99.97 | 0.00 | 0.01 | 0.02 |
| Raw Material Introduction | Reaction Product Composition (GC %) | | | |
| Integrated Amount (g) | 1284ze(E) | 1234zc | 245fa | 1234ze(Z) |
| 399 | 81.93 | 0.02 | 0.02 | 18.01 |
| 1,514 | 81.60 | 0.02 | 0.02 | 18.35 |
| 1,748 | 81.94 | 0.02 | 0.01 | 18.00 |
| 2,832 | 83.97 | 0.02 | 0.01 | 15.99 |
| 3,000 | 84.05 | 0.02 | 0.01 | 15.91 |
| 3,138 | 84.33 | 0.02 | 0.00 | 15.63 |
| 4,138 | 87.59 | 0.02 | 0.01 | 12.37 |

Comparative Example 1

The isomerization reaction was conducted similar to Example 1, except that E-1,3,3,3-tetrafluoropropene (moisture concentration: 133 ppm) with no dehydration treatment was used in place of the dehydrated E-1,3,3,3-tetrafluoropropene (moisture concentration: less than 1 ppm). The results are shown in Table 4.

TABLE 4

| Moisture Concentration | Raw Material Composition (GC %) | | | |
|---|---|---|---|---|
| 133 ppm | 1234ze(E) | 1234zc | 245fa | 1234ze(Z) |
| | 99.97 | 0.00 | 0.01 | 0.01 |
| Raw Material Introduction | Reaction Product Composition (GC %) | | | |
| Integrated Amount (g) | 1234ze(E) | 1234zc | 245fa | 1234ze(Z) |
| 72 | 81.63 | 0.03 | 0.03 | 18.30 |
| 259 | 81.61 | 0.03 | 0.01 | 18.31 |
| 423 | 82.95 | 0.03 | 0.00 | 16.99 |
| 1,556 | 85.28 | 0.03 | 0.00 | 14.68 |
| 1,642 | 87.89 | 0.03 | 0.00 | 12.05 |
| 1,928 | 88.77 | 0.03 | 0.00 | 11.18 |

Example 4

The isomerization reaction was conducted similar to Example 1, except that E-1,3,3,3-tetrafluoropropene (moisture concentration: 1.5 ppm) subjected to the dehydration treatment similar to Example 1 was used and that Catalyst 2 prepared by Preparation Example 2 was used in place of Catalyst 1. The results are shown in Table 5.

TABLE 5

| Moisture Concentration | Raw Material Composition (GC %) | | | |
|---|---|---|---|---|
| 1.5 ppm | 1234ze(E) | 1234zc | 245fa | 1234ze(Z) |
| | 99.97 | 0.00 | 0.01 | 0.01 |
| Raw Material Introduction | Reaction Product Composition (GC %) | | | |
| Integrated Amount (g) | 1234ze(E) | 1234zc | 245fa | 1234ze(Z) |
| 318 | 81.11 | 0.03 | 0.01 | 18.85 |
| 521 | 81.14 | 0.03 | 0.01 | 18.82 |
| 2,696 | 81.32 | 0.03 | 0.01 | 18.64 |
| 3,079 | 81.17 | 0.03 | 0.01 | 18.79 |
| 3,300 | 81.26 | 0.04 | 0.01 | 18.69 |
| 4,650 | 81.14 | 0.03 | 0.01 | 18.81 |
| 5,103 | 81.16 | 0.04 | 0.01 | 18.78 |
| 6,352 | 81.18 | 0.03 | 0.01 | 18.77 |

Example 5

The isomerization reaction was conducted similar to Example 4, except that moisture-adjusted E-1,3,3,3-tetrafluoropropene (moisture concentration: 47 ppm) was used in place of the dehydrated E-1,3,3,3-tetrafluoropropene (moisture concentration: 1.5 ppm). The results are shown in Table 6.

TABLE 6

| Moisture Concentration | Raw Material Composition (GC %) | | | |
|---|---|---|---|---|
| 47 ppm | 1234ze(E) | 1234zc | 245fa | 1234ze(Z) |
| | 99.97 | 0.00 | 0.01 | 0.02 |
| Raw Material Introduction | Reaction Product Composition (GC %) | | | |
| Integrated Amount (g) | 1234ze(E) | 1234zc | 245fa | 1234ze(Z) |
| 18 | 82.19 | 0.03 | 0.07 | 17.70 |
| 1,023 | 81.44 | 0.03 | 0.07 | 18.45 |
| 2,587 | 81.65 | 0.03 | 0.03 | 18.28 |
| 2,843 | 81.59 | 0.03 | 0.04 | 18.32 |
| 3,181 | 81.68 | 0.03 | 0.03 | 18.25 |
| 4,460 | 82.43 | 0.03 | 0.02 | 17.52 |
| 5,741 | 82.57 | 0.03 | 0.01 | 17.38 |
| 7,399 | 83.04 | 0.03 | 0.01 | 16.91 |

Comparative Example 2

The isomerization reaction was conducted similar to Example 4, except that E-1,3,3,3-tetrafluoropropene (moisture concentration: 129 ppm) with no dehydration treatment was used in place of the dehydrated E-1,3,3,3-tetrafluoropropene (moisture concentration: 1.5 ppm). The results are shown in Table 7.

TABLE 7

| Moisture Concentration | Raw Material Composition (GC %) | | | |
|---|---|---|---|---|
| 129 ppm | 1234ze(E) | 1234zc | 245fa | 1234ze(Z) |
| | 99.99 | 0.00 | 0.00 | 0.00 |
| Raw Material Introduction | Reaction Product Composition (GC %) | | | |
| Integrated Amount (g) | 1234ze(E) | 1234zc | 245fa | 1234ze(Z) |
| 152 | 84.78 | 0.03 | 0.02 | 15.17 |
| 278 | 86.78 | 0.03 | 0.01 | 13.17 |
| 400 | 87.72 | 0.03 | 0.01 | 12.23 |
| 768 | 89.08 | 0.04 | 0.00 | 10.87 |
| 802 | 88.62 | 0.04 | 0.00 | 10.33 |

Figure 1:
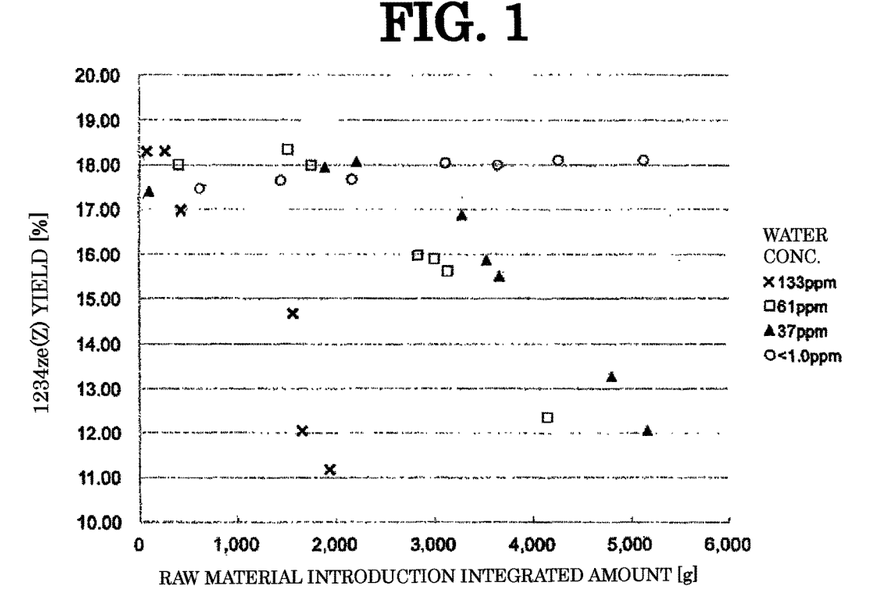
FIG. 1 is a graph showing relationships between the introduced integrated amounts of E-1,3,3,3-tetrafluoropropene as the introduced raw material and the yields of Z-1,3,3,3-tetrafluoropropene as the target material in Examples 1 to 3 and Comparative Example 1.
Figure 2:
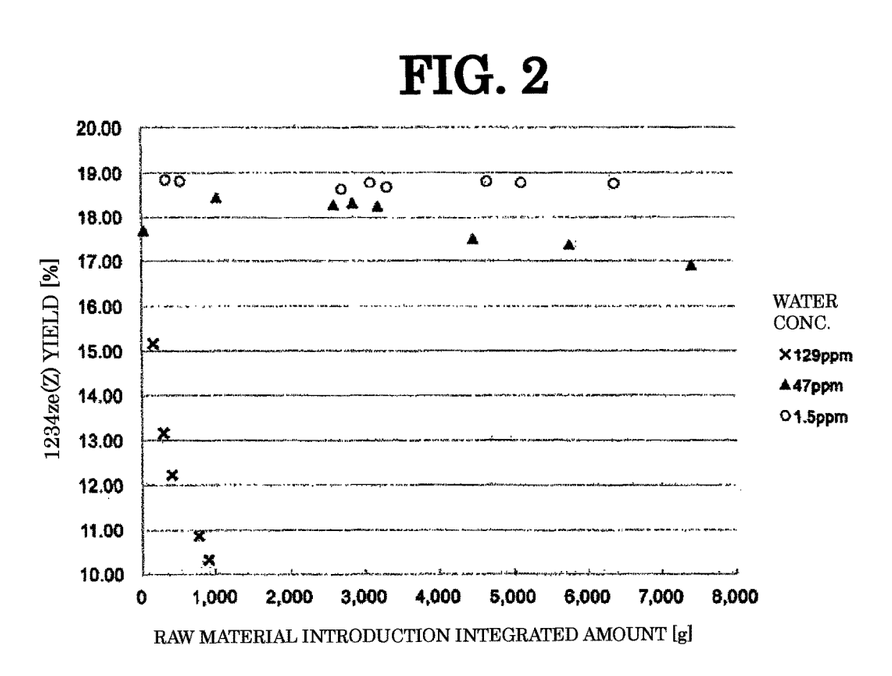
FIG. 2 is a graph showing relationships between the introduced integrated amounts of E-1,3,3,3-tetrafluoropropene as the introduced raw material and the yields of Z-1,3,3,3-tetrafluoropropene as the target material in Examples 4 to 5 and Comparative Example 2.

FIG. 1 shows the results prepared by plotting yields of Z-1,3,3,3-tetrafluoropropene at the points (the raw material introduction integrated amounts) when certain quantities of the raw material were introduced in Examples 1 to 3 and Comparative Example 1. FIG. 2 shows the results prepared by plotting similarly in Examples 4 to 5 and Comparative Example 2.

As shown in FIG. 1, when E-1,3,3,3-tetrafluoropropene having a moisture concentration of less than 1 ppm was used as the raw material, no lowering of yield of Z-1,3,3,3-tetrafluoropropene as the target material was found, and therefore deactivation of the catalyst was not found. Even in the case of using those having water concentrations of 37 ppm and 61 ppm, the catalyst performance was maintained, although some yield lowering was found as the raw material introduction integrated amount increased. However, in the case of using one having a moisture concentration of 133 ppm, yield lowering was found from an early stage after starting the raw material introduction, and therefore the catalyst performance lowered significantly.

Similarly, as shown in FIG. 2., when E-1,3,3,3-tetrafluoropropene having a moisture concentration of 1.5 ppm was used as the raw material, no lowering of yield of Z-1,3,3,3-tetrafluoropropene as the target material was found, and therefore deactivation of the catalyst was not found. Even in the case of using one having a water concentration of 47 ppm, lowering of yield of Z-1,3,3,3-tetrafluoropropene as the target material was almost not found, and therefore the catalyst performance was maintained. However, in the case of using one having a moisture concentration of 129 ppm, yield lowering was found from an early stage after starting the raw material introduction, and therefore the catalyst performance lowered significantly.

Example 6

A dehydration treatment was conducted by putting 1 kg of ZEOLUM A-3 (made by Tosoh Corporation) as a dehydrating agent into a sealed container filled with 10 kg of Z-1-chloro-3,3,3-trifluoropropene and then allowing it to stand still for one day. As moisture concentration of Z-1-chloro-3,3,3-trifluoropropene after the dehydration treatment was measured by a Karl Fisher moisture meter, it was 2.0 ppm. Herein, a moisture microanalyzer (made by Mitsubishi Chemical Analytech Co., Ltd., CA-200 type) was used as the Karl Fisher moisture meter, and a predetermined amount of a liquid sample was injected into the moisture meter with a syringe.

Then, 50 mL of Catalyst 2 prepared by Preparation Example 2 was loaded into a stainless steel (SUS 316L) reaction tube having a cylindrical shape (diameter: 2 cm; length: 40 cm) and equipped with an electric furnace. While nitrogen gas was allowed to flow at a flow rate of about 20 mL/minute, the temperature in the reaction tube was increased to 60° C.

Next, Z-1-chloro-3,3,3-trifluoropropene (moisture concentration: 2.0 ppm) resulting from the above-mentioned dehydration treatment was previously vaporized, and its supply to the reaction tube was started at a rate calculated based on the time (180 seconds) of contact with the catalyst. When the flow rate of the organic matter became stable, the introduction of nitrogen gas was stopped.

The gas mixture discharged from the exit of the reaction tube was bubbled into water to remove an acid gas. Then, the obtained product was analyzed by gas chromatography. The results are shown in Table 8. In the table, 1233zd(Z), 244fa, 1233zd(E), and others respectively represents Z-1-chloro-3, 3,3-trifluoropropene, 3-chloro-1,1,1,3-tetrafluoropropane, E-1-chloro-3,3,3-trifluoropropene, compounds of trace amounts except these three compounds. The same shall apply in the following.

TABLE 8

| Moisture Concentration | Raw Material Composition (GC %) | | | |
|---|---|---|---|---|
| 2.0 ppm | 1233zd(Z) | 244fa | 1233zd(E) | Others |
|  | 99.71 | 0.17 | 0.08 | 0.04 |
| Raw Material Introduction | Reaction Product Composition (GC %) | | | |
| Integrated Amount (g) | 1233zd(Z) | 244fa | 1233zd(E) | Others |
| 14 | 2.83 | 0.01 | 96.33 | 0.83 |
| 148 | 4.90 | 0.19 | 94.46 | 0.46 |
| 257 | 7.54 | 0.26 | 91.88 | 0.32 |
| 399 | 11.84 | 0.19 | 87.64 | 0.33 |
| 452 | 17.32 | 0.21 | 82.19 | 0.28 |
| 537 | 22.42 | 0.21 | 77.02 | 0.33 |

Comparative Example 3

The isomerization reaction was conducted similar to Example 6, except that Z-1-chloro-3,3,3-trifluoropropene (moisture concentration: 120 ppm) with no dehydration treatment was used in place of the dehydrated Z-1-chloro-3,3,3-trifluoropropene (moisture concentration: 2.0 ppm). The results are shown in Table 9.

TABLE 9

| Moisture Concentration | Raw Material Composition (GC %) | | | |
|---|---|---|---|---|
| 120 ppm | 1233zd(Z) | 244fa | 1233zd(E) | Others |
|  | 99.71 | 0.16 | 0.07 | 0.06 |
| Raw Material Introduction | Reaction Product Composition (GC %) | | | |
| Integrated Amount (g) | 1233zd(Z) | 244fa | 1233zd(E) | Others |
| 8 | 3.11 | 0.02 | 96.53 | 0.34 |
| 28 | 5.25 | 0.14 | 94.29 | 0.32 |

TABLE 9-continued

| 80 | 9.64 | 0.23 | 89.79 | 0.34 |
|---|---|---|---|---|
| 246 | 30.45 | 0.25 | 68.90 | 0.40 |
| 370 | 39.17 | 0.22 | 60.29 | 0.32 |
| 492 | 57.06 | 0.24 | 42.46 | 0.24 |

Example 7

50 mL of Catalyst 2 prepared by Preparation Example 2 was loaded into a stainless steel (SUS 316L) reaction tube having a cylindrical shape (diameter: 2 cm; length: 40 cm) and equipped with an electric furnace. While nitrogen gas was allowed to flow at a flow rate of about 20 mL/minute, the temperature in the reaction tube was increased to 200° C.

Next, Z-1-chloro-3,3,3-trifluoropropene (moisture concentration: 4.5 ppm) resulting from the above-mentioned dehydration treatment was previously vaporized, and its supply to the reaction tube was started at a rate calculated based on the time (60 seconds) of contact with the catalyst. When the flow rate of the organic matter became stable, the introduction of nitrogen gas was stopped.

The gas mixture discharged from the exit of the reaction tube was bubbled into water to remove an acid gas. Then, the obtained product was analyzed by gas chromatography. The results are shown in Table 10.

TABLE 10

| Moisture Concentration | Raw Material Composition (GC %) | | | |
|---|---|---|---|---|
| 4.5 ppm | 1233zd(Z) | 244fa | 1233zd(E) | Others |
|  | 99.71 | 0.17 | 0.08 | 0.04 |
| Raw Material Introduction | Reaction Product Composition (GC %) | | | |
| Integrated Amount (g) | 1233zd(Z) | 244fa | 1233zd(E) | Others |
| 19 | 9.20 | 0.03 | 90.24 | 0.53 |
| 71 | 7.28 | 0.01 | 91.25 | 0.76 |
| 381 | 7.09 | 0.00 | 92.31 | 0.60 |
| 584 | 8.00 | 0.01 | 91.42 | 0.57 |
| 779 | 8.07 | 0.01 | 91.48 | 0.44 |
| 1,020 | 8.14 | 0.01 | 91.37 | 0.48 |
| 1,257 | 11.06 | 0.02 | 88.50 | 0.42 |

Comparative Example 4

The isomerization reaction was conducted similar to Example 7, except that Z-1-chloro-3,3,3-trifluoropropene (moisture concentration: 130 ppm) with no dehydration treatment was used in place of the dehydrated Z-1-chloro-3,3,3-trifluoropropene (moisture concentration: 4.5 ppm). The results are shown in Table 11.

TABLE 11

| Moisture Concentration | Raw Material Composition (GC %) | | | |
|---|---|---|---|---|
| 130 ppm | 1233d(Z) | 244fa | 1233zd(E) | Others |
|  | 99.71 | 0.17 | 0.08 | 0.04 |
| Raw Material Introduction | Reaction Product Composition (GC %) | | | |
| Integrated Amount (g) | 1233zd(Z) | 244fa | 1233zd(E) | Others |
| 15 | 7.83 | 0.01 | 91.52 | 0.64 |
| 204 | 7.87 | 0.01 | 91.49 | 0.63 |
| 574 | 28.29 | 0.07 | 71.24 | 0.40 |
| 601 | 35.25 | 0.09 | 64.25 | 0.41 |

TABLE 11-continued

| | | | | |
|---|---|---|---|---|
| 688 | 57.46 | 0.12 | 42.23 | 0.19 |
| 937 | 85.59 | 0.19 | 14.02 | 0.20 |
| 1,039 | 96.10 | 0.21 | 3.50 | 0.19 |

Figure 3:
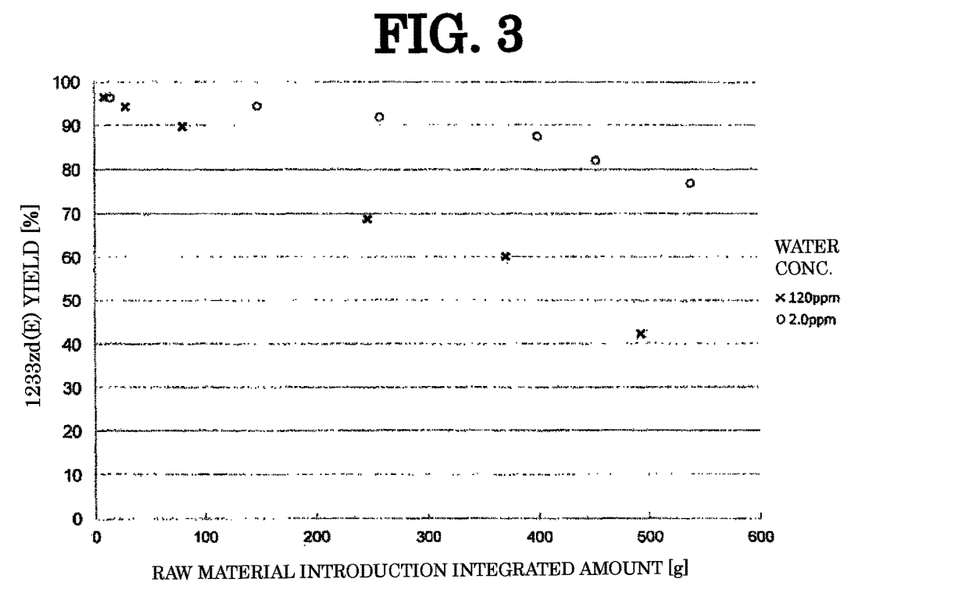
FIG. 3 is a graph showing relationships between the introduced integrated amounts of Z-1-chloro-3,3,3-trifluoropropene as the introduced raw material and the yields of E-1-chloro-3,3,3-trifluoropropene as the target material in Example 6 and Comparative Example 3.
Figure 4:
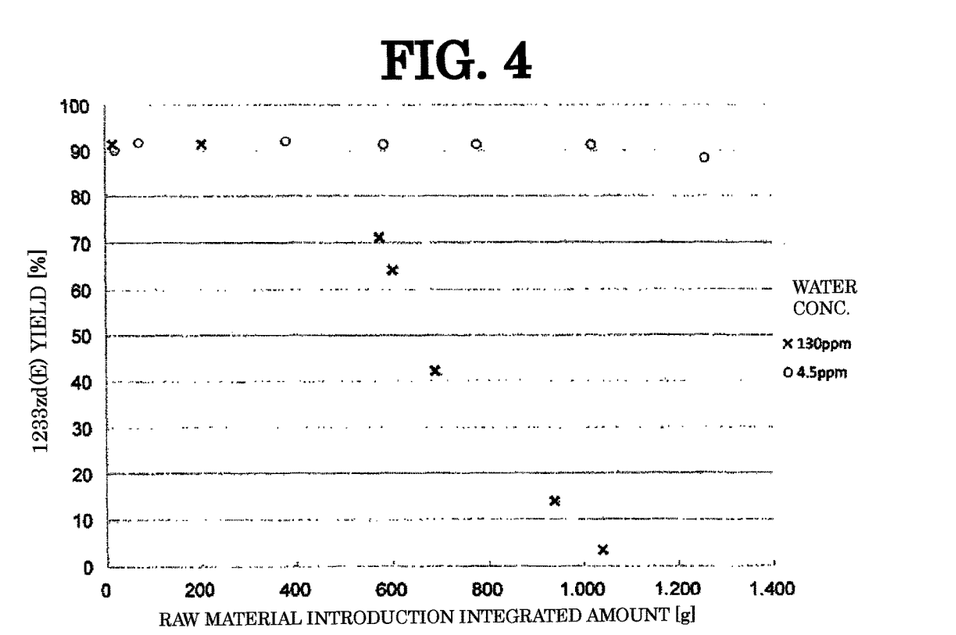
FIG. 4 is a graph showing relationships between the introduced integrated amounts of Z-1-chloro-3,3,3-trifluoropropene as the introduced raw material and the yields of E-1-chloro-3,3,3-trifluoropropene as the target material in Example 7 and Comparative Example 4.

FIG. 3 shows the results prepared by plotting yields of E-1-chloro-3,3,3-trifluoropropene at the points (the raw material introduction integrated amounts) when certain quantities of the raw material were introduced in Example 6 and Comparative Example 3. FIG. 4 shows the results prepared by plotting similarly in Example 7 and Comparative Example 4.

As shown in FIG. 3, when Z-1-chloro-3,3,3-trifluoropropene having a moisture concentration of 2.0 ppm was used as the raw material, the catalyst performance was maintained, although some yield lowering was found as the raw material introduction integrated amount increased. However, in the case of using one having a moisture concentration of 120 ppm, yield lowering was found from an early stage after starting the raw material introduction, and therefore the catalyst performance lowered significantly.

Similarly, as shown in FIG. 4., when Z-1-chloro-3,3,3-trifluoropropene having a moisture concentration of 4.5 ppm was used as the raw material, no lowering of yield of E-1-chloro-3,3,3-trifluoropropene as the target material was found, and therefore deactivation of the catalyst was not found. In the case of using one having a moisture concentration of 130 ppm, yield was maintained immediately after starting the introduction of the raw material, but after that yield lowering was found, and the catalyst performance lowered significantly.

Example 8

By a pump, 20 kg of Z-1,3,3,3-tetrafluoropropene in the form of liquid was delivered to and circulated through a drying tower filled with 200 g of ZEOLUM A-3 (made by Tosoh Corporation) as a dehydrating agent to conduct a dehydration treatment. As moisture concentration of Z-1,3,3,3-tetrafluoropropene after the dehydration treatment was measured by a Karl Fisher moisture meter equipped with a vaporizer, it was 2.4 ppm. Herein, a moisture microanalyzer (made by Mitsubishi Chemical Analytech Co., Ltd., CA-200 type) was used as the Karl Fisher moisture meter. A liquefied gas vaporizer (made by the same company; model number: VG-200 type) was connected to the sample introducing section. The sample of a predetermined amount was vaporized and automatically injected to the moisture meter.

Then, 50 mL of Catalyst 2 prepared by Preparation Example 2 was loaded into a stainless steel (SUS 316L) reaction tube having a cylindrical shape (diameter: 2 cm; length: 40 cm) and equipped with an electric furnace. While nitrogen gas was allowed to flow at a flow rate of about 20 mL/minute, the temperature in the reaction tube was increased to 200° C.

Next, Z-1,3,3,3-tetrafluoropropene (moisture concentration: 2.4 ppm) resulting from the above-mentioned dehydration treatment was previously vaporized, and its supply to the reaction tube was started at a rate calculated based on the time (60 seconds) of contact with the catalyst. When the flow rate of the organic matter became stable, the introduction of nitrogen gas was stopped.

The gas mixture discharged from the exit of the reaction tube was bubbled into water to remove an acid gas. Then, the obtained product was analyzed by gas chromatography. The results are shown in Table 12. In the table, 1234ze(E), 1234zc, 245fa and 1234ze(Z) respectively represent E-1,3,3-tetrafluoropropene, 1,1,3,3-tetrafluoropropene, 1,1,1,3,3-pentafluoropropane, and Z-1,3,3,3-tetrafluoropropene. The same shall apply in the following.

TABLE 12

| Moisture Concentration | Raw Material Composition (GC %) | | | |
|---|---|---|---|---|
| 2.4 ppm | 1234ze(E) | 1234zc | 245fa | 1234ze(Z) |
| | 0.00 | 0.03 | 0.00 | 99.97 |
| Raw Material Introduction | Reaction Product Composition (GC %) | | | |
| Integrated Amount (g) | 1234ze(E) | 1234zc | 245fa | 1234ze(Z) |
| 18 | 85.26 | 0.01 | 0.04 | 14.69 |
| 93 | 85.29 | 0.01 | 0.03 | 14.67 |
| 338 | 85.30 | 0.01 | 0.02 | 14.67 |
| 543 | 85.33 | 0.01 | 0.05 | 14.61 |
| 790 | 85.33 | 0.01 | 0.02 | 14.64 |
| 890 | 85.35 | 0.01 | 0.02 | 14.62 |
| 1,134 | 85.56 | 0.01 | 0.02 | 14.41 |
| 1,232 | 86.60 | 0.01 | 0.02 | 14.37 |

Comparative Example 5

The isomerization reaction was conducted similar to Example 8, except that Z-1,3,3,3-tetrafluoropropene (moisture concentration: 148 ppm) with no dehydration treatment was used in place of the dehydrated Z-1,3,3,3-tetrafluoropropene (moisture concentration: 2.4 ppm). The results are shown in Table 13.

TABLE 13

| Moisture Concentration | Raw Material Composition (GC %) | | | |
|---|---|---|---|---|
| 148 ppm | 1234ze(E) | 1234ze | 245fa | 1234ze(Z) |
| | 0.00 | 0.03 | 0.00 | 99.97 |
| Raw Material Introduction | Reaction Product Composition (GC %) | | | |
| Integrated Amount (g) | 1234ze(E) | 1234zc | 245fa | 1234ze(Z) |
| 32 | 85.13 | 0.01 | 0.2 | 14.65 |
| 253 | 84.60 | 0.01 | 0.1 | 15.29 |
| 300 | 83.12 | 0.01 | 0.09 | 16.77 |
| 614 | 71.77 | 0.01 | 0.03 | 28.18 |
| 877 | 45.80 | 0.02 | 0.02 | 54.15 |
| 892 | 41.48 | 0.02 | 0.01 | 58.48 |
| 911 | 29.57 | 0.02 | 0.01 | 70.39 |
| 933 | 24.43 | 0.02 | 0.01 | 75.53 |

Figure 5:
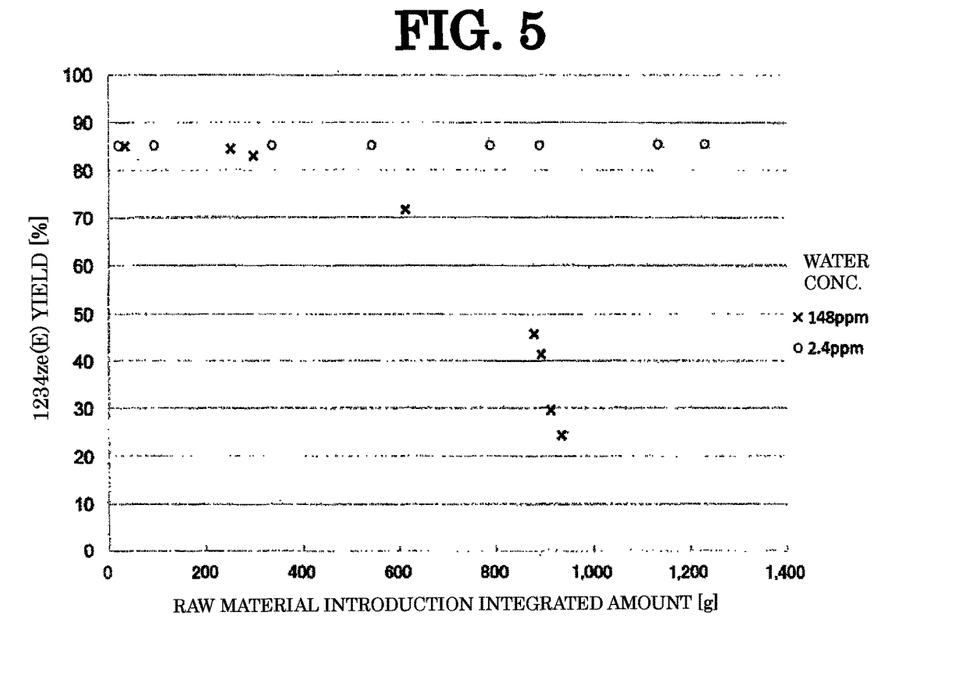
FIG. 5 is a graph showing relationships between the introduced integrated amounts of Z-1,3,3,3-tetrafluoropropene as the introduced raw material and the yields of E-1,3,3,3-tetrafluoropropene as the target material in Example 8 and Comparative Example 5.

FIG. 5 shows the results prepared by plotting yields of E-1,3,3,3-tetrafluoropropene at the points (the raw material introduction integrated amounts) when certain quantities of the raw material were introduced in Example 8 and Comparative Example 5.

As shown in FIG. 5, when Z-1,3,3,3-tetrafluoropropene having a moisture concentration of 2.4 ppm was used as the raw material, no lowering of yield of E-1,3,3,3-tetrafluoropropene as the target material was found, and therefore deactivation of the catalyst was not found. In the case of using one having a moisture concentration of 148 ppm, yield was maintained immediately after starting the introduction of the raw material, but after that yield lowering was found, and the catalyst performance lowered significantly.

From the results of the above-mentioned Examples 1 to 8 and Comparative Examples 1 to 5, it was clear that, if moisture introduced into the reaction system together with the raw material exceeds a certain concentration, a significant lowering of the catalyst performance is caused, irrespective of the substrate type and the isomer ratio.

The invention claimed is:

1. A method for isomerizing a hydrohalofluoroolefin isomer (isomer 1) to produce a corresponding hydrohalofluoroolefin isomer (isomer 2) by cis/transisomerization, comprising step 1 of contacting a composition that contains at least a hydrohalofluoroolefin isomer (isomer 1) and that has been adjusted to 100 ppm or lower in moisture concentration, with a catalyst in a gas phase, thereby obtaining a product comprising isomer 2.

2. The method according to claim 1, wherein there is used a composition that contains at least a hydrohalofluoroolefin isomer (isomer 1) and that has been adjusted to 50 ppm or lower in moisture concentration.

3. The method according to claim 1, wherein the contacting is conducted at a temperature of 0 to 600° C. with a contact time of 0.01 to 500 seconds.

4. The method according to claim 1, wherein the contacting is conducted at a temperature of 20 to 550° C. with a contact time of 1 to 150 seconds.

5. The method according to claim 3, wherein the temperature and the contact time are in a trade-off relation.

6. The method according to claim 1, wherein the catalyst is a metal oxide containing at least one metal selected from the group consisting of aluminum, chromium, titanium, manganese, iron, nickel, cobalt, copper, magnesium, zirconium, molybdenum, zinc, tin, lanthanum, niobium, tantalum, and antimony.

7. The method according to claim 1, wherein the catalyst is a metal fluorinated compound that has been partially or totally fluorinated and that contains at least one metal selected from the group consisting of aluminum, chromium, titanium, manganese, iron, nickel, cobalt, copper, magnesium, zirconium, molybdenum, zinc, tin, lanthanum, niobium, tantalum, and antimony.

8. The method according to claim 1, wherein the catalyst is a supported catalyst that supports a metal compound containing at least one metal selected from the group consisting of aluminum, chromium, titanium, manganese, iron, nickel, cobalt, copper, magnesium, zirconium, molybdenum, zinc, tin, lanthanum, niobium, tantalum, and antimony.

9. The method according to claim 6, wherein the catalyst is a catalyst that has been further subjected to a fluorination treatment.

10. The method according to claim 1, wherein the hydrohalofluoroolefin isomer (isomer 1) is a hydrohalofluoroolefin containing two to six carbons.

11. The method according to claim 1, wherein the hydrohalofluoroolefin isomer (isomer 1) is a hydrohalofluoroolefin represented by the following general formula (1)

$$(CX^1X^2X^3)CX^4\!=\!CX^5X^6 \qquad (1)$$

wherein each of $X^1$ to $X^6$ is independently H, F, Cl or Br, and, of $X^1$ to $X^6$, one to five of them are fluorines, the rest is H, Cl or Br, and at least one of them is H.

12. The method according to claim 1, wherein the hydrohalofluoroolefin isomer (isomer 1) is 1-chloro-3,3,3-trifluoropropene, 1,2-dichloro-3,3,3-trifluoropropene, 1,3,3,3-tetrafluoropropene, 1-chloro-1,3,3,3-tetrafluoropropene, 2-chloro-1,3,3,3-tetrafluoropropene, 1-chloro-2,3,3,3-tetrafluoropropene, or 1,2,3,3,3-pentafluoropropene.

13. The method according to claim 1, further comprising step 2 of removing an acid component comprising hydrogen fluoride from the product obtained by step 1 and then separating the hydrohalofluoroolefin isomer (isomer 2) from the product from which the acid component has been removed.

14. The method according to claim 1, wherein the product obtained by step 1 contains the hydrohalafluoroolefin isomer (isomer 1), the method further comprising:

step 3 of removing an acid component comprising hydrogen fluoride from the product obtained by step 1 and then separating a composition that contains at least the hydrohalofluoroolefin isomer (isomer 1) from the product from which the acid component has been removed; and step 4 of reusing the composition that contains at least the hydrohalofluoroolefin isomer (isomer 1) and that has been separated by step 3, as the composition containing at least the hydrohalofluoroolefin isomer (isomer 1) of step 1.

15. The method according to claim 1, wherein the moisture concentration adjustment is conducted by distilling the composition containing at least the hydrohalofluoroolefin isomer (isomer 1), or by contacting the composition containing at least the hydrohalofluoroolefin isomer (isomer 1) with a dehydrating agent, or by both of the distilling and the contacting.

16. The method according to claim 15, wherein the moisture concentration adjustment is conducted by distilling the composition containing at least the hydrohalofluoroolefin isomer (isomer 1), and, at least prior to the distillation, contacting the composition containing at least the hydrohalofluoroolefin isomer (isomer 1) with a dehydrating agent.

17. The method according to claim 1, wherein the hydrohalofluoroolefin isomer (isomer 1) is E-1-chloro-3,3,3-trifluoropropene, Z-1,3,3,3-tetrafluoropropene, or E-1,3,3,3-tetrafluoropropene.

18. A method for contacting a hydrohalofluoropropene isomer (isomer 1) of the general formula (3) with a catalyst to produce a corresponding hydrohalofluoropropene isomer (isomer 2), by cis/trans isomerization, comprising contacting a composition that contains at least a hydrohalofluoropropene isomer (isomer 1) and that has been adjusted to 100 ppm or lower in moisture concentration, with a catalyst in a gas phase at a temperature of 0 to 600° C. with a contact time of 0.01 to 500 seconds $$CF_3CH\!=\!CHX^7 \qquad (3)$$

wherein $X^7$ is F or Cl.

19. The method according to claim 18, wherein the catalyst is a metal fluorinated compound that has been partially or totally fluorinated and that contains at least one metal selected from the group consisting of aluminum, chromium, titanium, manganese, iron, nickel, cobalt, copper, magnesium, zirconium, molybdenum, zinc, tin, lanthanum, niobium, tantalum, and antimony.

20. The method according to claim 18, wherein the hydrohalofluoropropene isomer (isomer 1) of the general formula (3) is E isomer, and wherein the contacting is conducted at a temperature of 200 to 550° C. with a contact time of 0.1 to 250 seconds.

21. The method according to claim 18, wherein the hydrohalofluoropropene isomer (isomer 1) of the general formula (3) is Z isomer, and wherein the contacting is conducted at a temperature of 50 to 300° C. with a contact time of 15 to 200 seconds.

22. The method according to claim 20, wherein the temperature and the contact time are in a trade-off relation.

23. The method according to claim 18, wherein the hydrohalofluoroolefin isomer (isomer ) is E-1-3,3,3-trifluoropropene, Z-1,3,3,3,-tetrafluoroprone, or E-1,3,3,3-tetrafluoropropene.

24. A method for isomerizing a hydrohalofluoroolefin isomer (isomer 1) by a contact with a catalyst in a gas phase to produce a corresponding hydrohalofluoroolefin isomer (isomer 2), by is/trans isomerization, comprising:
  adjusting a moisture concentration of a composition containing at least a hydrohalofluoroolefin isomer (isomer 1) to 100 ppm or lower; and
  supplying the composition to an isomerization reaction system.

25. The metrod according to claim 24, wherein the hydrohalofluoroolefin isomer )isomer 1) is E-1-chloro-3,3,3,-trifluoropropene, Z1,3,3,3,-tetrafluoropropene, or E-1,3,3,3-tetrafluoroprone.

* * * * *